(12) United States Patent
Suzuki et al.

(10) Patent No.: US 8,378,146 B2
(45) Date of Patent: Feb. 19, 2013

(54) METHOD FOR PRODUCING CATECHOL

(75) Inventors: Tsuneji Suzuki, Chiba (JP); Takaomi Hayashi, Chiba (JP); Hideo Kitagawa, Kawasaki (JP); Naritoshi Yoshimura, Funabashi (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 205 days.

(21) Appl. No.: 12/936,269

(22) PCT Filed: Apr. 7, 2009

(86) PCT No.: PCT/JP2009/001607
§ 371 (c)(1),
(2), (4) Date: Oct. 4, 2010

(87) PCT Pub. No.: WO2009/125581
PCT Pub. Date: Oct. 15, 2009

(65) Prior Publication Data
US 2011/0034735 A1    Feb. 10, 2011

(30) Foreign Application Priority Data
Apr. 11, 2008   (JP) ................................ 2008-104034

(51) Int. Cl.
C07C 45/00    (2006.01)
C07C 33/30    (2006.01)
(52) U.S. Cl. ....................................... 568/338; 568/811
(58) Field of Classification Search .................. 568/338, 568/811
See application file for complete search history.

(56) References Cited

PUBLICATIONS

Marco-Contelles et al. Recent results in the free radical mediated synthesis of enantiomerically pure, highly functionalized carbocycles from carbohydrates. Comptes Rendus de l' Academie des Sciences, Serie IIc: Chimie, 2001, 4 (6), 443-452; HCAPLUS Document No. 135:288988.*
International Search Report (PCT/ISA/210) issued on Jun. 23, 2009, by Japanese Patent Office as thr International Searching Authority for International Application No. PCT/JP2009/001607.
Katsumi Kakinuma et al., An expeditious chemo-enzymatic route from glucose to catechol by the use of 2-deoxy-scylio-inosose synthase, Tetrahedron Letters 41, 2000, pp. 1935-1938, Tokyo Japan.
Andre Lubineau, et al., Synthesis of polyhydroxylated cyclohexenyl sulfoxides. Evaluation of their inhibitory activity on α- and β-D-glucosidases, Carbohydrate Research 320, 1999, pp. 49-60, Orsay, France.
K.M. Draths, et al., Environmentally Compatible Synthesis of Catechol from D-Glucose, J. Am. Chem. Soc., 1995, 117, pp. 2395-2400, East Lansing, Michigan, USA.
Chad A. Hansen, et al., Deoxygenation of Polyhydroxybenzenes: An Alternative Strategy for the Benzene-Free Synthesis of Aromatic Chemicals, J. Am. Chem. Soc, 2002, 124, pp. 5926-5927, East Lansing, Michigan, USA.

* cited by examiner

*Primary Examiner* — Sikarl Witherspoon
(74) *Attorney, Agent, or Firm* — Buchanan Ingersoll & Rooney PC

(57) ABSTRACT

Provided is a method for producing catechol in a one-pot by reacting (4S,5R,6S)-4,5,6-trihydroxy-2-cyclohexene-1-one under hydrogen-reducing conditions while heating.

19 Claims, No Drawings

METHOD FOR PRODUCING CATECHOL

TECHNICAL FIELD

The present invention relates to a novel method for producing catechol from 2-deoxy-scyllo-inosose via an intermediate of (4S,5R,6S)-4,5,6-trihydroxy-2-cyclohexene-1-one.

BACKGROUND ART

Catechol is a general-purpose substance which has been used as a raw material for polymerization inhibitors, pharmaceutical products, agricultural chemicals, perfumes and the like, or as an oxidation inhibitor or a rubber vulcanizer, and is produced mainly by oxidizing phenol with hydrogen peroxide. However, in late years, from the viewpoints of escalating prices or a problem of exhaustion of fossil resources, and reduction of the emission of carbon dioxide as greenhouse gas, catechol is one of the chemicals which has been earnestly desired to be produced from renewable resources.

Various attempts have already been made. For example, as disclosed in Non-patent Document 1, there has been known a method for obtaining catechol at a yield of 33% from D-glucose via shikimic acid by microorganisms.

Furthermore, as disclosed in Non-patent Document 2, there has been known a method for obtaining catechol at a yield of 59% by conducting a reductive dehydration reaction with hydroiodic acid in acetic acid from D-glucose via 2-deoxy-scyllo-inosose.

Non-patent Document 1: J. Am. Chem. Soc. K. M. Draths and J. W. Frost, 1995, 117, pp. 2395-2400

Non-patent Document 2: Tetrahedron Letters, Katsumi Kakinuma et. al, 2000, 41, pp. 1935-1938

Non-patent Document 3: J. Am. Chem. Soc. C. A. Hansen and J. W. Frost, 2002, 124, pp. 5926-5927

Non-patent Document 4: Carbohydrate Research A. Lubineau and I. Billault, 1999, 320, pp. 49-60

DISCLOSURE OF THE INVENTION

However, there is a problem in Non-patent Document 2 such that expensive and highly corrosive hydroiodic acid must be used in large quantities. Accordingly, special facilities are needed due to its corrosive property so that it is not easy to industrially produce catechol.

Under the above circumstances, the present invention aims to enable the production of catechol that is a commodity chemical in an industrially suitable manner.

According to the present invention, there is provided a method for producing catechol from (4S,5R,6S)-4,5,6-trihydroxy-2-cyclohexene-1-one represented by the following formula (1).

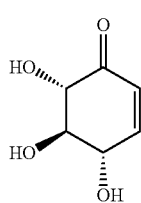

(1)

The present invention comprises the following embodiments.

(1) The method for producing catechol as described above, by dehydrating 2-deoxy-scyllo-inosose represented by the following formula (2) to produce (4S,5R,6S)-4,5,6-trihydroxy-2-cyclohexene-1-one, and further conducting hydrogenation and dehydration reactions of the (4S,5R,6S)-4,5,6-trihydroxy-2-cyclohexene-1-one.

[Chemical Formula 2]

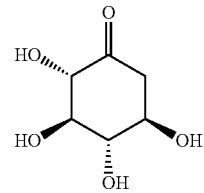

(2)

(2) The method for producing catechol as described above, by reacting 2-deoxy-scyllo-inosose under hydrogen-reducing conditions while heating via (4S,5R,6S)-4,5,6-trihydroxy-2-cyclohexene-1-one.

(3) The method for producing catechol as described above, by reacting (4S,5R,6S)-4,5,6-trihydroxy-2-cyclohexene-1-one under hydrogen-reducing conditions while heating.

(4) The method for producing catechol as described above, by dehydrating 2-deoxy-scyllo-inosose to produce (4S,5R,6S)-4,5,6-trihydroxy-2-cyclohexene-1-one, and further reacting the (4S,5R,6S)-4,5,6-trihydroxy-2-cyclohexene-1-one under hydrogen-reducing conditions while heating.

(5) The method for producing catechol as described above, by reacting (4S,5R,6S)-4,5,6-trihydroxy-2-cyclohexene-1-one in the presence of a metal catalyst.

(6) The method for producing catechol as described above, wherein the metal catalyst contains a metal selected from the group consisting of platinum group metals or the group consisting of iron group metals.

(7) The method for producing catechol as described above, wherein the metal catalyst contains palladium.

(8) The method for producing catechol as described above, wherein a metal component contained in the metal catalyst is loaded in activated carbon, alumina or zeolite.

(9) The method for producing catechol as described above, by reacting (4S,5R,6S)-4,5,6-trihydroxy-2-cyclohexene-1-one in an aqueous solution.

(10) The method for producing catechol as described above, in a one-pot from 2-deoxy-scyllo-inosose.

(11) The method for producing catechol as described above, from 2-deoxy-scyllo-inosose in the presence of a solid acid.

(12) The method for producing catechol as described above, wherein the solid acid is selected from the group consisting of zeolite, activated clay and Nafion (registered trademark).

(13) The method for producing catechol as described above, by reducing (4S,5R,6S)-4,5,6-trihydroxy-2-cyclohexene-1-one with hydrogen to produce (2S,3R,4S)-2,3,4-trihydroxycyclohexane-1-one represented by the following formula (3), and dehydrating the (2S,3R,4S)-2,3,4-trihydroxycyclohexane-1-one.

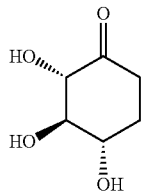

(3)

(14) The method for producing catechol as described above, by dehydrating 2-deoxy-scyllo-inosose while heating to give (4S,5R,6S)-4,5,6-trihydroxy-2-cyclohexene-1-one, and then reducing the (4S,5R,6S)-4,5,6-trihydroxy-2-cyclohexene-1-one with hydrogen in the presence of a metal catalyst to give (2S,3R,4S)-2,3,4-trihydroxycyclohexane-1-one, and then further dehydrating the (2S,3R,4S)-2,3,4-trihydroxycyclohexane-1-one while heating.

Furthermore, according to the present invention, there is provided a method for producing (4S,5R,6S)-4,5,6-trihydroxy-2-cyclohexene-1-one by dehydrating 2-deoxy-scyllo-inosose.

Furthermore, according to the present invention, there is provided (4S,5R,6S)-4,5,6-trihydroxy-2-cyclohexene-1-one.

Furthermore, according to the present invention, there is provided a method for producing catechol by dehydrating (2S,3R,4S)-2,3,4-trihydroxycyclohexane-1-one while heating.

Furthermore, according to the present invention, there is provided a method for producing (2S,3R,4S)-2,3,4-trihydroxycyclohexane-1-one by reducing (4S,5R,6S)-4,5,6-trihydroxy-2-cyclohexene-1-one with hydrogen.

Furthermore, according to the present invention, there is provided a method for producing catechol by reacting 2,3,4,5-tetrahydroxy-cyclohexane-1-one represented by the following formula (4) under hydrogen-reducing conditions while heating.

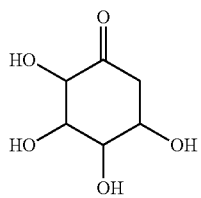

(4)

According to the present invention, it is possible to produce catechol from (4S,5R,6S)-4,5,6-trihydroxy-2-cyclohexene-1-one. According to this method, it is possible to produce catechol by reduction of olefin in (4S,5R,6S)-4,5,6-trihydroxy-2-cyclohexene-1-one and by dehydration of two molecules of water. Accordingly, it is possible to obtain catechol under mild conditions without using a corrosive reagent, and to achieve the production of catechol suitable for industrial production with less load to the environment.

According to the present invention, it is possible to produce catechol that is a commodity chemical by the method suitable for industrial production with less load to the environment.

BEST MODE FOR CARRYING OUT THE INVENTION

The present invention will be described in more detail below.

First Embodiment

The present embodiment relates to a method for producing catechol from (4S,5R,6S)-4,5,6-trihydroxy-2-cyclohexene-1-one represented by the following formula (1).

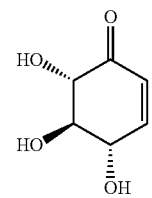

(1)

According to this method, catechol is produced by the reaction represented by the formula (5).

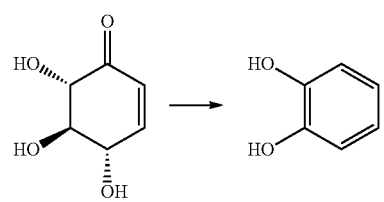

(5)

Specifically, the present embodiment relates to a method for producing catechol by reacting (4S,5R,6S)-4,5,6-trihydroxy-2-cyclohexene-1-one under hydrogen-reducing conditions while heating.

In the present embodiment, catechol is produced in a one-pot from (4S,5R,6S)-4,5,6-trihydroxy-2-cyclohexene-1-one. "One-pot" mentioned herein means that a number of reactions are conducted in the same reaction vessel, specifically, referring to a reduction reaction and a dehydration reaction.

When catechol is produced from (4S,5R,6S)-4,5,6-trihydroxy-2-cyclohexene-1-one, the reaction "under hydrogen-reducing conditions" refers to the reaction of (4S,5R,6S)-4,5,6-trihydroxy-2-cyclohexene-1-one dissolved in a solvent in the presence of a reduction catalyst under hydrogen atmosphere.

The solvent is not particularly limited as long as it does not hinder the progress of the reaction. Examples thereof include water or alcohol solvents such as methanol, ethanol, butanol and the like; hydrocarbon solvents such as hexane, toluene, xylene and the like; ester solvents such as ethyl acetate, butyl acetate and the like; ether solvents such as diisopropyl ether, dioxane, ethylene glycol dimethyl ether, tetrahydrofuran and the like; halogen solvents such as chloroform, dichloromethane and the like; acetonitrile, dimethylformamide, dimethyl sulfoxide and the like. These solvents can be used singly or two or more kinds can be used as a mixed solvent at any ratio. However, it is preferable to use water.

The concentration of (4S,5R,6S)-4,5,6-trihydroxy-2-cyclohexene-1-one to be introduced is not particularly restricted. However, it is preferably, for example, equal to or more than 1 w/v % and equal to or less than 30 w/v %.

"While heating" mentioned in the present embodiment means an increase of the reaction temperature to an atmospheric temperature or higher, and as necessary, also contains the concept of change of the temperature as the time elapses during the reaction. By changing the temperature, the reaction can proceed step by step. The reaction temperature is usually in the range of equal to or more than 30 degrees centigrade and equal to or less than 300 degrees centigrade. When the reaction temperature is low, the reaction rate of the dehydration reaction is reduced. When the reaction temperature is high, the side reaction proceeds. Accordingly, by heating at a temperature of equal to or more than 30 degrees centigrade and equal to or less than 300 degrees centigrade, catechol can be produced with good efficiency. The reaction temperature is more preferably equal to or more than 35 and equal to or less than 240 degrees centigrade and further preferably equal to or more than 70 and equal to or less than 200 degrees centigrade. Thus, it is possible to make the dehydration reaction to proceed at a suitable reaction rate, and to produce catechol with better efficiency.

The reaction time is not particularly limited, but it is from several minutes to 48 hours and preferably in the range of 30 minutes to 24 hours. Thus, it is possible to surely conduct reduction and dehydration of (4S,5R,6S)-4,5,6-trihydroxy-2-cyclohexene-1-one, and to produce catechol with good efficiency.

As the reduction catalyst, there can be used metals selected from platinum group metals such as palladium, rhodium, ruthenium, platinum, iridium and the like, and from iron group metals such as nickel, cobalt and the like; and metals such as copper and the like. These metals may be used singly or may be loaded in activated carbon, silica gel, alumina, graphite, diatomaceous earth, pumice, montmorillonite, zeolite or the like. Concrete examples include palladium/activated carbon, palladium/silica gel, palladium/alumina, palladium/zeolite, nickel/alumina, copper/alumina, ruthenium/activated carbon, rhodium/activated carbon, platinum/activated carbon, iridium/activated carbon and the like. Furthermore, the amount of the metal loaded is usually in the range of 0.01 to 50 weight % based on the carrier. Thus, it is possible to make the reduction reaction to suitably proceed. The amount of the reduction catalyst added is preferably in the range of 0.1 to 10 weight %.

"Under hydrogen atmosphere" means a reaction performed in a reactor filled with gas containing hydrogen of from atmospheric pressure to 10 MPa, and is preferably between atmospheric pressure and 1 MPa. Hydrogen may be used singly or in mixture with nitrogen or the like.

A method for producing (4S,5R,6S)-4,5,6-trihydroxy-2-cyclohexene-1-one will be described later, but (4S,5R,6S)-4,5,6-trihydroxy-2-cyclohexene-1-one can be produced by dehydrating 2-deoxy-scyllo-inosose.

Furthermore, the reaction can be conducted by heating even in the absence of a catalyst, but an additive can be added for the reaction in order to promote the reaction. As the additive, there can be used an acid, a base or salts thereof.

Examples of the acid in use include inorganic acids such as hydrogen chloride, hydrogen bromide, sulfuric acid, phosphoric acid and the like; organic acids such as formic acid, acetic acid, propionic acid, oxalic acid, citric acid, lactic acid, benzoic acid, trifluoroacetic acid, p-toluenesulfonic acid, methanesulfonic acid, dodecylbenzenesulfonic acid and the like; and solid acids such as zeolite, silica gel, alumina, activated clay, Nafion (registered trademark), ion exchange resin and the like. The amount of the acid added is preferably in the range of 1 to 2,000 weight %.

Examples of the base in use include inorganic bases such as lithium hydroxide, sodium hydroxide, potassium hydroxide, sodium carbonate, potassium carbonate, sodium hydrogen carbonate and the like; and organic amine bases such as triethylamine, pyridine, 1,8-diazabicycloundecene and the like.

As a method for obtaining catechol after the completion of the reaction, a reduction catalyst or an inhomogeneous additive is removed from the reaction solution by filtration, and then the filtrate is concentrated, whereby crude purified catechol can be obtained as a crystal. Crude purified catechol can be purified by distillation or recrystallization to obtain much purified catechol. Or the heated reaction solution is cooled after conducting solvent concentration to some extent to precipitate catechol as a crystal, whereby catechol can be obtained by filtration. A solvent which hardly dissolves catechol is added to precipitate catechol as a crystal, whereby catechol can also be obtained by filtration. Further, a suitable solvent can be added to the reaction solvent to extract. The extract is treated in the same manner as above, whereby much purified catechol can be obtained.

Next, the effect of the present embodiment will be described. The present inventors have conducted an extensive study and as a result, have found that catechol is easily obtained by conducting hydrogenation and dehydration reactions of (4S,5R,6S)-4,5,6-trihydroxy-2-cyclohexene-1-one obtained from 2-deoxy-scyllo-inosose.

According to the method in the present embodiment, since (4S,5R,6S)-4,5,6-trihydroxy-2-cyclohexene-1-one is reacted under hydrogen atmosphere while heating, it is possible to conduct by hydrogen-addition reduction and dehydration reactions at the same time in a one-pot. Accordingly, ideally, catechol can be produced by using hydrogen in a molar amount equivalent to a substrate, and a catalyst in a small amount. Accordingly, it is possible to produce catechol at a low cost under mild conditions without using a corrosive reagent. Thus, it is possible to achieve the production of catechol suitable for industrial production with ease.

Second Embodiment

The present embodiment relates to a method for producing catechol by dehydrating 2-deoxy-scyllo-inosose represented by the following formula (2) to produce (4S,5R,6S)-4,5,6-trihydroxy-2-cyclohexene-1-one and further conducting hydrogenation and dehydration reactions of the (4S,5R,6S)-4,5,6-trihydroxy-2-cyclohexene-1-one. According to this method, catechol is produced by the reaction represented by the formula (6).

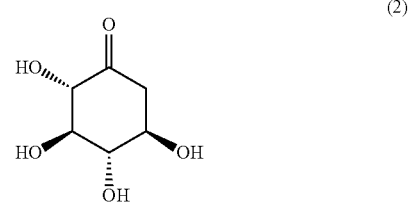

(2)

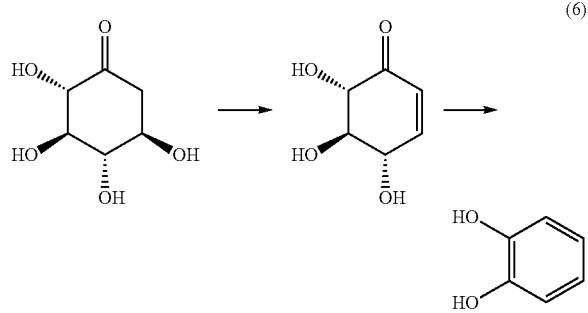

Specifically, catechol is produced in a one-pot by reacting 2-deoxy-scyllo-inosose under hydrogen-reducing conditions while heating via (4S,5R,6S)-4,5,6-trihydroxy-2-cyclohexene-1-one.

In this method, 2-deoxy-scyllo-inosose is dehydrated to produce (4S,5R,6S)-4,5,6-trihydroxy-2-cyclohexene-1-one which is further reacted under hydrogen-reducing conditions while heating, whereby catechol is produced.

In the present embodiment, catechol is produced in a one-pot from 2-deoxy-scyllo-inosose.

In the present embodiment, when catechol is produced from 2-deoxy-scyllo-inosose via (4S,5R,6S)-4,5,6-trihydroxy-2-cyclohexene-1-one, "reacting under hydrogen-reducing conditions while heating" refers to the reaction of 2-deoxy-scyllo-inosose dissolved in a solvent in the presence of a reduction catalyst under hydrogen atmosphere while heating.

The solvent is not particularly limited as long as it does not hinder the progress of the reaction. Examples thereof include water or alcohol solvents such as methanol, ethanol, butanol and the like; hydrocarbon solvents such as hexane, toluene, xylene and the like; ester solvents such as ethyl acetate, butyl acetate and the like; ether solvents such as diisopropyl ether, dioxane, ethylene glycol dimethyl ether, tetrahydrofuran and the like; halogen solvents such as chloroform, dichloromethane and the like; acetonitrile, dimethylformamide, dimethyl sulfoxide and the like. These solvents can be used singly or two or more kinds can be used as a mixed solvent at any ratio. However, it is preferable to use water.

The concentration of 2-deoxy-scyllo-inosose to be introduced is not particularly restricted, but it is preferably, for example, equal to or more than 1 w/v % and equal to or less than 30 w/v %.

"While heating" mentioned in the present embodiment means an increase of the reaction temperature to an atmospheric temperature or higher, and as necessary, also contains the concept of change of the temperature as the time elapses during the reaction. By changing the temperature, the reaction can proceed step by step. The reaction temperature is usually in the range of equal to or more than 30 degrees centigrade and equal to or less than 300 degrees centigrade. When the reaction temperature is low, the reaction rate of the dehydration reaction is reduced. When the reaction temperature is high, the side reaction proceeds. Accordingly, by heating at a temperature of equal to or more than 30 degrees centigrade and equal to or less than 300 degrees centigrade, catechol can be produced with good efficiency. The reaction temperature is more preferably equal to or more than 60 degrees centigrade and equal to or less than 240 degrees centigrade and further preferably equal to or more than 70 degrees centigrade and equal to or less than 200 degrees centigrade. Thus, it is possible to make the dehydration reaction to proceed at a suitable reaction rate, and to produce catechol with better efficiency.

The reaction time is not particularly limited, but it is from several minutes to 48 hours and preferably in the range of 1 to 24 hours. Thus, it is possible to surely conduct dehydration of 2-deoxy-scyllo-inosose and reduction of an intermediate of (4S,5R,6S)-4,5,6-trihydroxy-2-cyclohexene-1-one, and to produce catechol with good efficiency.

As the reduction catalyst, there can be used metals selected from platinum group metals such as palladium, rhodium, ruthenium, platinum, iridium and the like, and from iron group metals such as nickel, cobalt and the like; and metals such as copper and the like. These metals may be used singly or may be loaded in activated carbon, silica gel, alumina, graphite, diatomaceous earth, pumice, montmorillonite, zeolite or the like. Concrete examples include palladium/activated carbon, palladium/silica gel, palladium/alumina, palladium/zeolite, nickel/alumina, copper/alumina, ruthenium/activated carbon, rhodium/activated carbon, platinum/activated carbon, iridium/activated carbon and the like. Furthermore, the amount of the metal loaded is usually in the range of 0.01 to 50 weight % based on the carrier. Thus, it is possible to make the reduction reaction to suitably proceed. The amount of the reduction catalyst added is preferably in the range of 0.1 to 10 weight %.

"Under hydrogen atmosphere" means a reaction performed in a reactor filled with gas containing hydrogen of from atmospheric pressure to 10 MPa, and is preferably between atmospheric pressure and 1 MPa. Hydrogen may be used singly or in mixture with nitrogen or the like.

Furthermore, the reaction can be conducted by heating even in the absence of a catalyst, but an additive can be added for the reaction in order to promote the reaction. As the additive, there can be used an acid, a base or salts thereof.

Examples of the acid in use include inorganic acids such as hydrogen chloride, hydrogen bromide, sulfuric acid, phosphoric acid and the like; organic acids such as formic acid, acetic acid, propionic acid, oxalic acid, citric acid, lactic acid, benzoic acid, trifluoroacetic acid, p-toluenesulfonic acid, methanesulfonic acid, dodecylbenzenesulfonic acid and the like; and solid acids such as zeolite, silica gel, alumina, activated clay, Nafion (registered trademark), ion exchange resin and the like. The amount of the acid added is preferably in the range of 1 to 2,000 weight %.

Examples of the base in use include inorganic bases such as lithium hydroxide, sodium hydroxide, potassium hydroxide, sodium carbonate, potassium carbonate, sodium hydrogen carbonate and the like; and organic amine bases such as triethylamine, pyridine, 1,8-diazabicycloundecene and the like.

Furthermore, "one-pot" mentioned herein means that a number of reactions are conducted in the same reaction vessel, specifically, referring to a reduction reaction and a dehydration reaction.

Incidentally, 2-deoxy-scyllo-inosose used in the present embodiment obtained from D-glucose by fermentation has been known by Non-patent Document 2, Non-patent Document 3 and WO 2006/112000.

As a method for obtaining catechol after the completion of the reaction, a reduction catalyst or an inhomogeneous additive is removed from the reaction solution by filtration, and then the filtrate is concentrated, whereby crude purified catechol can be obtained as a crystal. Crude purified catechol can be purified by distillation or recrystallization to obtain much purified catechol. Or the heated reaction solution is cooled after conducting solvent concentration to some extent to precipitate catechol as a crystal, whereby catechol can be obtained by filtration. A solvent which hardly dissolves catechol is added to precipitate catechol as a crystal, whereby catechol can also be obtained by filtration. Further, a suitable solvent can be added to the reaction solvent to extract. The extract is treated in the same manner as above, whereby much purified catechol can be obtained.

Next, the effect of the present embodiment will be described.

According to the present embodiment, it is possible to obtain catechol by reacting 2-deoxy-scyllo-inosose under hydrogen-reducing conditions while heating in a one-pot. Thus, catechol can be produced from D-glucose that is a renewable resource at a low cost without using a corrosive reagent. Accordingly, it is possible to achieve the production of catechol suitable for industrial production.

According to the present embodiment, it is possible to obtain catechol by reacting 2-deoxy-scyllo-inosose easily obtained from a renewable resource of glucose by fermentation under hydrogen-reducing conditions while heating via (4S,5R,6S)-4,5,6-trihydroxy-2-cyclohexene-1-one. Accordingly, catechol can be easily produced by conducting hydrogen-addition reduction and dehydration reactions at the same time in a one-pot.

In Non-patent Document 2 as described above, there has been known a method for obtaining catechol at a yield of 59% by conducting a reductive dehydration reaction of 2-deoxy-scyllo-inosose in acetic acid by hydrogen iodide. However, this reaction requires 2 molecules of hydrogen iodide for 2-deoxy-scyllo-inosose. That is, catechol is considered to be generated by attaching 1 molecule of hydrogen iodide to a carbonyl group and subsequently reacting with the other 1 molecule of hydrogen iodide to reduce 2-deoxy-scyllo-inosose by eliminating iodine and water, and further conducting dehydration. Accordingly, there is a problem such that 2 equivalents of hydroiodic acid which is highly corrosive and expensive must be used even in an ideal reaction.

On the other hand, in the method of the present embodiment, ideally, hydrogen in a molar amount equivalent to a substrate and a catalyst in a small amount are only required. Further, because of (4S,5R,6S)-4,5,6-trihydroxy-2-cyclohexene-1-one passing through, catechol can be synthesized under mild conditions. Accordingly, it is possible to produce catechol at a low cost with ease without using a corrosive reagent, and to achieve the production of catechol suitable for industrial production.

Meanwhile, in the method of the present embodiment, it is possible to conduct the hydrogen reduction reaction using a metal catalyst. Accordingly, the material cost becomes cheaper so that the method is favorable for industrial production. Since a corrosive reagent in large quantities is not used, this method is also good to the environment.

According to the method in the present embodiment, it is possible to produce catechol in a one-pot by reacting 2-deoxy-scyllo-inosose. Accordingly, there is no need to conduct isolation and purification in each step so that the method is further favorable for industrial production.

Furthermore, according to the method in the present embodiment, it is possible to produce catechol that is a commodity chemical by using 2-deoxy-scyllo-inosose easily produced from glucose, i.e., a renewable resource, or the like as a raw material. Thus, it is useful for the decrease of use of fossil resources, suppression of discharge of greenhouse gas and prevention of global warming.

Third Embodiment

The present embodiment relates a method for producing catechol in which 2-deoxy-scyllo-inosose is dehydrated while heating to give (4S,5R,6S)-4,5,6-trihydroxy-2-cyclohexene-1-one, and then the (4S,5R,6S)-4,5,6-trihydroxy-2-cyclohexene-1-one is reduced with hydrogen in the presence of a metal catalyst to give (2S,3R,4S)-2,3,4-trihydroxycyclohexane-1-one represented by the following formula (3), and then the (2S,3R,4S)-2,3,4-trihydroxycyclohexane-1-one is dehydrated while heating. In the method of this Embodiment, catechol is produced by the reaction represented by the formula (7).

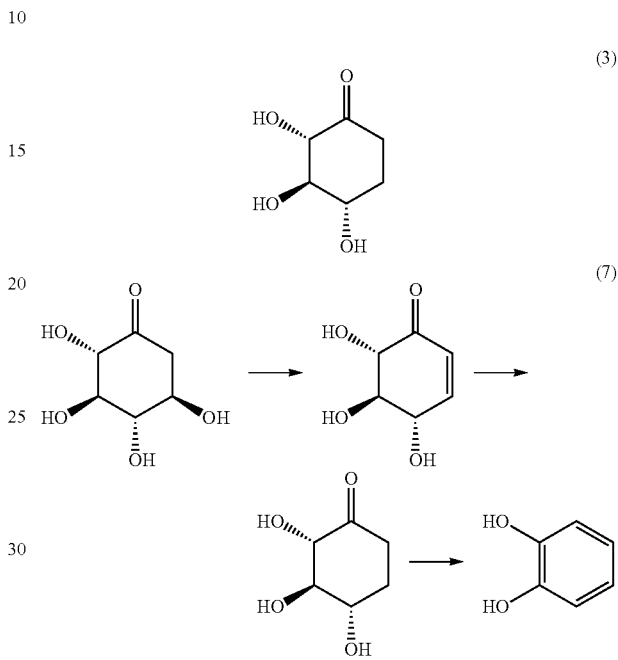

In the second embodiment, a method for producing catechol in a one-pot was illustrated. In the present embodiment, the following three processes are respectively conducted to produce catechol:
(First process) a process of producing (4S,5R,6S)-4,5,6-trihydroxy-2-cyclohexene-1-one from 2-deoxy-scyllo-inosose;
(Second process) a process of producing (2S,3R,4S)-2,3,4-trihydroxycyclohexane-1-one from (4S,5R,6S)-4,5,6-trihydroxy-2-cyclohexene-1-one; and
(Third process) a process of producing catechol from (2S,3R,4S)-2,3,4-trihydroxycyclohexane-1-one.
<First Process>

The first process is a process of producing (4S,5R,6S)-4,5,6-trihydroxy-2-cyclohexene-1-one by dehydrating 2-deoxy-scyllo-inosose.

When (4S,5R,6S)-4,5,6-trihydroxy-2-cyclohexene-1-one is produced by dehydrating 2-deoxy-scyllo-inosose, the reaction temperature can be equal to or more than 30 degrees centigrade and equal to or less than 300 degrees centigrade. When the reaction temperature is low, the reaction rate of the dehydration reaction is reduced. When the reaction temperature is high, the side reaction proceeds. Accordingly, by heating at a temperature of equal to or more than 30 degrees centigrade and equal to or less than 300 degrees centigrade, (4S,5R,6S)-4,5,6-trihydroxy-2-cyclohexene-1-one can be produced with good efficiency. The reaction temperature is more preferably in the range of equal to or more than 100 degrees centigrade and equal to or less than 240 degrees centigrade. Thus, it is possible to make the dehydration reaction to proceed at a suitable reaction rate, and to produce (4S,5R,6S)-4,5,6-trihydroxy-2-cyclohexene-1-one with better efficiency.

The solvent is not particularly limited as long as it does not hinder the progress of the reaction. Examples thereof include water or alcohol solvents such as methanol, ethanol, butanol and the like; hydrocarbon solvents such as hexane, toluene, xylene and the like; ester solvents such as ethyl acetate, butyl acetate and the like; ether solvents such as diisopropyl ether, dioxane, ethylene glycol dimethyl ether, tetrahydrofuran and the like; halogen solvents such as chloroform, dichloromethane and the like; acetonitrile, dimethylformamide, dimethyl sulfoxide and the like. These solvents can be used singly or two or more kinds can be used as a mixed solvent at any ratio. However, it is preferable to use water.

The reaction time is not particularly limited, but it is from several minutes to 48 hours and preferably in the range of 15 minutes to 24 hours. Thus, it is possible to surely conduct dehydration of 2-deoxy-scyllo-inosose, and to produce (4S,5R,6S)-4,5,6-trihydroxy-2-cyclohexene-1-one with good efficiency.

The reaction can be conducted by heating even in the absence of a catalyst. However, as an additive in order to promote the reaction, there can be used an acid, a base or salts thereof.

Examples of the acid in use include inorganic acids such as hydrogen chloride, hydrogen bromide, sulfuric acid, phosphoric acid and the like; organic acids such as formic acid, acetic acid, propionic acid, oxalic acid, citric acid, lactic acid, benzoic acid, trifluoroacetic acid, p-toluenesulfonic acid, methanesulfonic acid, dodecylbenzenesulfonic acid and the like; and solid acids such as zeolite, silica gel, alumina, activated clay, Nafion (registered trademark), an ion exchange resin and the like. The amount of the acid added is preferably in the range of 1 to 2,000 weight %.

Examples of the base in use include inorganic bases such as lithium hydroxide, sodium hydroxide, potassium hydroxide, sodium carbonate, potassium carbonate, sodium hydrogen carbonate and the like; and organic amine bases such as triethylamine, pyridine, 1,8-diazabicycloundecene and the like.

However, as disclosed in Non-patent Document 3, when two molecules of water are dehydrated from 2-deoxy-scyllo-inosose, 1,2,4-trihydroxybenzene is generated. Accordingly, in order to obtain (4S,5R,6S)-4,5,6-trihydroxy-2-cyclohexene-1-one in high yield, the reaction temperature, reaction time and catalyst need to be controlled. More specifically, when the reaction is conducted at a high temperature, the reaction is conducted with a weak catalyst or in the absence of a catalyst within a short period of time, or when the reaction is conducted at a low temperature, the reaction is conducted using a strong catalyst for a long period of time, whereby generation of 1,2,4-trihydroxybenzene can be suppressed.

Incidentally, the catalyst refers to an additive exemplified in acids or bases. In case of using a catalyst of the same kind, the catalyst can be reacted as a strong catalyst by increasing the concentration in a catalyst solution, or can be reacted as a weak catalyst by lowering the concentration in a catalyst solution. Furthermore, in case of using a catalyst of the different kind, for example, as pH of a solution containing water as a solvent is far from 7, the catalyst can act as a strong catalyst, while as pH is close to 7, it can act as a weak catalyst. The reaction temperature and time are controlled while properly changing the catalyst, whereby (4S,5R,6S)-4,5,6-trihydroxy-2-cyclohexene-1-one can be synthesized with good efficiency.

Furthermore, 2-deoxy-scyllo-inosose used for the present invention is available as described in the second embodiment.

For (4S,5R,6S)-4,5,6-trihydroxy-2-cyclohexene-1-one after the completion of the reaction, it is possible to obtain a crude product by concentrating the reaction solution. As necessary, pH can be adjusted to near the neutrality (pH of 6 to 8). Also, when an inhomogeneous additive is used, the additive is removed from the reaction solution by filtration and the filtrate is concentrated in the same manner, whereby a crude purified product can be obtained. Further, the crude purified product is purified by recrystallization or silica gel column, whereby it is possible to obtain high purity (4S,5R,6S)-4,5,6-trihydroxy-2-cyclohexene-1-one.

<Second Process>

The second process is a process of producing (2S,3R,4S)-2,3,4-trihydroxycyclohexane-1-one by reducing (4S,5R,6S)-4,5,6-trihydroxy-2-cyclohexene-1-one with hydrogen in the presence of a metal catalyst.

As the metal catalyst mentioned herein, there can be used metals selected from platinum group metals such as palladium, rhodium, ruthenium, platinum, iridium or the like, and from iron group metals such as nickel, cobalt or the like; and metals such as copper and the like. These metals may be used singly or may be loaded in activated carbon, silica gel, alumina, graphite, diatomaceous earth, pumice, montmorillonite, zeolite or the like. Concrete examples thereof include palladium/activated carbon, palladium/silica gel, palladium/alumina, palladium/zeolite, nickel/alumina, copper/alumina, ruthenium/activated carbon, rhodium/activated carbon, platinum/activated carbon, iridium/activated carbon and the like. The amount of the metal loaded is usually in the range of 0.01 to 50 weight % based on the carrier. The amount of the reduction catalyst added is preferably in the range of 0.1 to 10 weight %.

"Under hydrogen atmosphere" means a reaction performed in a reactor filled with gas containing hydrogen of from atmospheric pressure to 10 MPa, and is preferably between atmospheric pressure and 1 MPa. Hydrogen may be used singly or in mixture with nitrogen or the like.

The solvent is not particularly limited as long as it does not hinder the progress of the reaction. Examples thereof include water or alcohol solvents such as methanol, ethanol, butanol and the like; hydrocarbon solvents such as hexane, toluene, xylene and the like; ester solvents such as ethyl acetate, butyl acetate and the like; ether solvents such as diisopropyl ether, dioxane, ethylene glycol dimethyl ether, tetrahydrofuran and the like; halogen solvents such as chloroform, dichloromethane and the like; acetonitrile, dimethylformamide, dimethyl sulfoxide and the like. These solvents can be used singly or two or more kinds can be used as a mixed solvent at any ratio. However, the dehydration reaction can be suppressed by using methanol so that (2S,3R,4S)-2,3,4-trihydroxycyclohexane-1-one can be produced with good efficiency; therefore, methanol is preferable.

The concentration of (4S,5R,6S)-4,5,6-trihydroxy-2-cyclohexene-1-one to be introduced is not particularly restricted. However, it is preferably, for example, equal to or more than 1 w/v % and equal to or less than 30 w/v %.

Meanwhile, an additive can be added for the reaction in order to promote the reaction. As the additive, there can be used an acid, a base or salts thereof.

Examples of the acid in use include inorganic acids such as hydrogen chloride, hydrogen bromide, sulfuric acid, phosphoric acid and the like; organic acids such as formic acid, acetic acid, propionic acid, oxalic acid, citric acid, lactic acid, benzoic acid, trifluoroacetic acid, p-toluenesulfonic acid, methanesulfonic acid, dodecylbenzenesulfonic acid and the like; and solid acids such as zeolite, silica gel, alumina, activated clay, Nafion (registered trademark), ion exchange resin and the like. The amount of the acid added is preferably in the range of 1 to 2,000 weight %.

Examples of the base in use include inorganic bases such as lithium hydroxide, sodium hydroxide, potassium hydroxide, sodium carbonate, potassium carbonate, sodium hydrogen carbonate and the like; and organic amine bases such as triethylamine, pyridine, 1,8-diazabicycloundecene and the like.

The reaction can be conducted at a temperature of from room temperature (25 degrees centigrade) to 300 degrees centigrade, and preferably in the range of equal to or more than 60 degrees centigrade and equal to or less than 240 degrees centigrade. Thus, it is possible to make the reduction reaction to proceed at a suitable reaction rate, and to suppress the progress of the dehydration reaction. Accordingly, (2S,3R,4S)-2,3,4-trihydroxycyclohexane-1-one can be produced with better efficiency.

The reaction time is not particularly limited, but it is from several minutes to 48 hours and preferably in the range of 10 minutes to 24 hours. Thus, it is possible to surely conduct reduction of (4S,5R,6S)-4,5,6-trihydroxy-2-cyclohexene-1-one.

(2S,3R,4S)-2,3,4-trihydroxycyclohexane-1-one can be obtained by removing the reduction catalyst by filtration and concentrating the filtrate. As necessary, much higher purity (2S,3R,4S)-2,3,4-trihydroxycyclohexane-1-one can be obtained by recrystallization.

<Third Process>

The third process is a process of producing catechol by dehydrating (2S,3R,4S)-2,3,4-trihydroxycyclohexane-1-one while heating.

The solvent is not particularly limited as long as it does not hinder the progress of the reaction. Examples thereof include water or alcohol solvents such as methanol, ethanol, butanol and the like; hydrocarbon solvents such as hexane, toluene, xylene and the like; ester solvents such as ethyl acetate, butyl acetate and the like; ether solvents such as diisopropyl ether, dioxane, ethylene glycol dimethyl ether, tetrahydrofuran and the like; halogen solvents such as chloroform, dichloromethane and the like; acetonitrile, dimethylformamide, dimethyl sulfoxide and the like. These solvents can be used singly or two or more kinds can be used as a mixed solvent at any ratio. However, it is preferable to use water.

The concentration of (2S,3R,4S)-2,3,4-trihydroxycyclohexane-1-one to be introduced is not particularly restricted. However, it is preferably, for example, equal to or more than 1 w/v % and equal to or less than 30 w/v %.

Meanwhile, an additive can be added for the reaction in order to promote the reaction. As the additive, there can be used an acid, a base or salts thereof.

Examples of the acid in use include inorganic acids such as hydrogen chloride, hydrogen bromide, sulfuric acid, phosphoric acid and the like; organic acids such as formic acid, acetic acid, propionic acid, oxalic acid, citric acid, lactic acid, benzoic acid, trifluoroacetic acid, p-toluenesulfonic acid, methanesulfonic acid, dodecylbenzenesulfonic acid and the like; and solid acids such as zeolite, silica gel, alumina, activated clay, Nafion (registered trademark), ion exchange resin and the like. The amount of the acid added is preferably in the range of 1 to 2,000 weight %.

Examples of the base in use include inorganic bases such as lithium hydroxide, sodium hydroxide, potassium hydroxide, sodium carbonate, potassium carbonate, sodium hydrogen carbonate and the like; and organic amine bases such as triethylamine, pyridine, 1,8-diazabicycloundecene and the like.

"While heating" mentioned in the present embodiment means an increase of the reaction temperature to an atmospheric temperature or higher, and as necessary, also contains the concept of change of the temperature as the time elapses during the reaction. By changing the temperature, the reaction can proceed step by step. It refers to heating at a temperature of equal to or more than 30 degrees centigrade and equal to or less than 300 degrees centigrade. When the reaction temperature is low, the reaction rate is reduced. When the reaction temperature is high, the side reaction proceeds. Accordingly, by heating at a temperature of equal to or more than 30 degrees centigrade and equal to or less than 300 degrees centigrade, catechol can be produced. The reaction temperature is more preferably equal to or more than 60 degrees centigrade and equal to or less than 240 degrees centigrade and further preferably equal to or more than 70 degrees centigrade and equal to or less than 200 degrees centigrade. Thus, it is possible to make the dehydration reaction to proceed at a suitable reaction rate, and to produce catechol with better efficiency.

The reaction time is not particularly limited, but it is from several minutes to 48 hours and preferably in the range of 10 minutes to 24 hours. Thus, it is possible to surely conduct dehydration of (2S,3R,4S)-2,3,4-trihydroxycyclohexane-1-one.

As a method for obtaining catechol after the completion of the reaction, a reduction catalyst or an inhomogeneous additive is removed from the reaction solution by filtration, and then the filtrate is concentrated, whereby crude purified catechol can be obtained as a crystal. Crude purified catechol can be purified by distillation or recrystallization to obtain much purified catechol. Or the heated reaction solution is cooled after conducting solvent concentration to some extent to precipitate catechol as a crystal, whereby catechol can be obtained by filtration. A solvent which hardly dissolves catechol is added to precipitate catechol as a crystal, whereby catechol can also be obtained by filtration. Further, a suitable solvent can be added to the reaction solvent to extract. The extract is treated in the same manner as above, whereby much purified catechol can be obtained.

Next, the effect of the present embodiment will be described.

According to the present embodiment, 2-deoxy-scyllo-inosose is dehydrated and the obtained (4S,5R,6S)-4,5,6-trihydroxy-2-cyclohexene-1-one is reduced to give (2S,3R,4S)-2,3,4-trihydroxycyclohexane-1-one which is then dehydrated, whereby catechol can be obtained. Accordingly, catechol which is useful as a commodity chemical can be easily produced from renewable resources such as glucose or the like.

According to the method of the first process in the present embodiment, it is possible to produce (4S,5R,6S)-4,5,6-trihydroxy-2-cyclohexene-1-one by dehydrating 2-deoxy-scyllo-inosose while heating. Accordingly, it is possible to easily produce (4S,5R,6S)-4,5,6-trihydroxy-2-cyclohexene-1-one that is an important intermediate for the production of catechol which is useful as a commodity chemical.

More specifically, there has been known that 2-deoxy-scyllo-inosose is heated in a 0.5M phosphoric acid aqueous solution to dehydrate two molecules of water to give 1,2,4-trihydroxybenzene (Non-patent Document 3). However, 2-deoxy-scyllo-inosose is reacted by controlling the reaction temperature, time, catalyst and the like to dehydrate one molecule of water, whereby (4S,5R,6S)-4,5,6-trihydroxy-2-cyclohexene-1-one can be produced. That is, when the reaction is conducted at a high temperature, the reaction is conducted with a weak catalyst or in the absence of a catalyst within a short period of time, or when the reaction is conducted at a low temperature, the reaction is conducted using a strong catalyst for a long period of time, whereby generation of 1,2,4-trihydroxybenzene can be suppressed. Accordingly, it is possible to easily produce (4S,5R,6S)-4,5,6-trihydroxy-2-cyclohexene-1-one that is an important intermediate for the production of catechol which is useful as a commodity chemical.

According to the method of the second process in the present embodiment, it is possible to produce (2S,3R,4S)-2,3,4-trihydroxycyclohexane-1-one by reducing (4S,5R,6S)-4,5,6-trihydroxy-2-cyclohexene-1-one. Accordingly, it is possible to easily produce (2S,3R,4S)-2,3,4-trihydroxycyclohexane-1-one that is an important intermediate for the production of catechol which is useful as a commodity chemical.

In the past, there has been known (4R,5S,6R)-4,5,6-trihydroxy-2-cyclohexene-1-one having a configuration opposite to that of (4S,5R,6S)-4,5,6-trihydroxy-2-cyclohexene-1-one (Non-patent Document 4 and the like). However, a method for synthesizing (4S,5R,6S)-4,5,6-trihydroxy-2-cyclohexene-1-one has not been known. This substance is an intermediate useful for the purpose of production of catechol, and its double bonds are easily reduced with hydrogen in the presence of a catalyst to give (2S,3R,4S)-2,3,4-trihydroxycyclohexane-1-one and the (2S,3R,4S)-2,3,4-trihydroxycyclohexane-1-one is further dehydrated in the presence or absence of a catalyst, whereby catechol can be obtained. Accordingly, (4S,5R,6S)-4,5,6-trihydroxy-2-cyclohexene-1-one can be produced, so that it is possible to easily produce catechol which is useful as a commodity chemical.

According to the method of the third process in the present embodiment, catechol can be produced by dehydrating (2S,3R,4S)-2,3,4-trihydroxycyclohexane-1-one while heating. Accordingly, catechol which is useful as a commodity chemical can be produced from renewable resources such as glucose or the like.

Although the present invention has been described by way of embodiments as described above, such embodiments are exemplified in the present invention and other various constructions can also be adopted.

For example, the second embodiment and the third embodiment describe methods for producing catechol using 2-deoxy-scyllo-inosose as a starting material. However, 2,3,4,5-tetrahydroxy-cyclohexane-1-one represented by the following formula (4) can also be applied in place of 2-deoxy-scyllo-inosose.

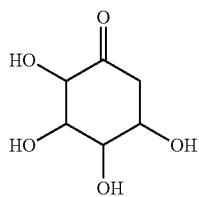

(4)

EXAMPLES

The present invention is now illustrated in detail below with reference to Examples. However, the present invention is not restricted to these Examples.

Example 1

Synthesis of catechol from 2-deoxy-scyllo-isonose>

150 mg of 2-deoxy-scyllo-inosose synthesized according to the method described in WO 2006/112000 was dissolved in 3 mL of 0.5 N acetic acid, and the resulting mixture was introduced into an autoclave. Furthermore, 3 mg (50 weight % of water contained) of weight % Pd/C (palladium/activated carbon) was introduced thereinto, and the reactor was replaced with nitrogen. The resulting material was heated to 100 degrees centigrade by applying hydrogen pressure of 0.35 MPa with stirring to conduct a hydrogenation reaction for 19 hours. After cooling, the reactor was replaced with nitrogen and a quantitative analysis was carried out using HPLC. As a result, the raw material was lost, and catechol was obtained at a yield of 56%.

Analysis conditions for HPLC: 10 mM acetic acid aqueous solution/acetonitrile=94/6, 1.2 mL/min., UV=220 nm, column in use; ODS-AQ, internal standard; methyl gallate.

Example 2

Synthesis of catechol from 2-deoxy-scyllo-inosose>

150 mg of 2-deoxy-scyllo-inosose synthesized according to the method described in WO 2006/112000 was dissolved in 3 mL of water, and the resulting mixture was introduced into an autoclave. Furthermore, 3 mg (50 weight % of water contained) of 5 weight % Pd/C was introduced thereinto, and the reactor was replaced with nitrogen. The resulting material was heated to 170 degrees centigrade by applying hydrogen pressure of 0.1 MPa with stirring to conduct a hydrogenation reaction. During the reaction, the reaction solution was collected and analyzed using HPLC and as a result, existence of (4S,5R,6S)-4,5,6-trihydroxy-2-cyclohexene-1-one was confirmed. The reaction was conducted for 4 hours in total for cooling, and then the reactor was replaced with nitrogen, and a quantitative analysis was carried out using HPLC. As a result, the raw material was lost, and catechol was obtained at a yield of 23%. Analysis conditions were the same as in Example 1.

Example 3

Synthesis of (4S,5R,6S)-4,5,6-trihydroxy-2-cyclohexene-1-one from 2-deoxy-scyllo-inosose 1.64 g of 2-deoxy-scyllo-inosose synthesized according to the method described in WO 2006/112000 and 5 mL of an ion exchange resin IR120B were added to 13.6 mL of water, and the resulting mixture was heated at reflux for 20 hours. After the completion of the reaction, the ion exchange resin was filtered and the filtrate was concentrated under a reduced pressure. The condensation residue was purified with silica gel column (ethyl acetate), whereby 604 mg (yield: 41%) of (4S,5R,6S)-4,5,6-trihydroxy-2-cyclohexene-1-one was obtained.

$^1$H-NMR (CD$_3$OD); δ6.91 (dd, 1H, J=2.3, 11.5 Hz), 6.02 (dd, 1H, J=2.7, 11.5 Hz), 4.35 (dt, J=2.3, 8.2 Hz), 3.57 (dd, 1H, J=8.2, 11.5 Hz)

$^{13}$C-NMR (CD$_3$OD); δ200.18, 153.32, 127.51, 79.93, 78.12, 73.06

Example 4

Synthesis of (2S,3R,4S)-2,3,4-trihydroxycyclohexane-1-one from (4S,5R,6S)-4,5,6-trihydroxy-2-cyclohexene-1-one 205 mg of (4S,5R,6S)-4,5,6-trihydroxy-2-cyclohexene-1-one obtained in Example 3 was dissolved in 3.5 mL of methanol. 20 mg (50 weight % of water contained) of 5 weight % Pd/C was added thereto and hydrogenated at room temperature (25 degrees centigrade) under ordinary pressure (1 atm). After the completion of the reaction, the catalyst was removed by filtration, and the filtrate was concentrated to obtain 198 mg (yield: 96%) of (2S,3R,4S)-2,3,4-trihydroxycyclohexane-1-one.

$^1$H-NMR (DMSO); δ5.21 (d, 1H, OH), 4.91 (d, 1H, OH), 4.87 (d, 1H, OH), 3.88 (m, 1H), 3.63 (m, 1H), 3.07 (m, 1H), 2.48 (m, 1H), 2.14 (m, 1H), 1.33 (m, 1H)

Example 5

Synthesis of Catechol from (2S,3R,4S)-2,3,4-trihydroxycyclohexane-1-one 29.2 mg of (2S,3R,4S)-2,3,4-trihydroxycyclohexane-1-one obtained in Example 4 was dissolved in 1 mL of 33 w/v % phosphoric acid aqueous solution, and the resulting mixture was heated at 100 degrees centigrade for 2 hours. A quantitative analysis was carried out using HPLC and as a result, catechol was obtained at a yield of 86%.

Analysis conditions for HPLC: 10 mM acetic acid aqueous solution/acetonitrile=94/6, 1.2 mL/min., UV=220 nm, column in use; ODS-AQ, internal standard; methyl gallate.

Example 6

Synthesis of (4S,5R,6S)-4,5,6-trihydroxy-2-cyclohexene-1-one from 2-deoxy-scyllo-inosose 0.15 g of 2-deoxy-scyllo-inosose synthesized according to the method described in WO 2006/112000 was added to 1.35 mL of 0.5 N acetic acid water, and the resulting mixture was heated at 120 degrees centigrade for 1 hour. After the completion of the reaction, a quantitative analysis was carried out using HPLC and as a result, (4S,5R,6S)-4,5,6-trihydroxy-2-cyclohexene-1-one was obtained at a yield of 33%. At this time, 44% of the raw material of 2-deoxy-scyllo-inosose was collected.

Analysis conditions for HPLC: 10 mM acetic acid aqueous solution/acetonitrile=94/6, 1.2 mL/min., UV=220 nm, column in use; ODS-AQ, internal standard; methyl gallate.

Example 7

Synthesis of (4S,5R,6S)-4,5,6-trihydroxy-2-cyclohexene-1-one from 2-deoxy-scyllo-inosose 0.05 g of 2-deoxy-scyllo-inosose synthesized according to the method described in WO 2006/112000 was added to 1 mL of 5 N acetic acid water, and the resulting mixture was heated at 100 degrees centigrade for 2 hours. After the completion of the reaction, a quantitative analysis was carried out using HPLC and as a result, (4S,5R,6S)-4,5,6-trihydroxy-2-cyclohexene-1-one was obtained at a yield of 48%. At this time, 35% of the raw material of 2-deoxy-scyllo-inosose was collected.

Analysis conditions for HPLC: 10 mM acetic acid aqueous solution/acetonitrile=94/6, 1.2 mL/min., UV=220 nm, column in use; ODS-AQ, internal standard; methyl gallate.

Example 8

Synthesis of (4S,5R,6S)-4,5,6-trihydroxy-2-cyclohexene-1-one from 2-deoxy-scyllo-inosose 0.5 g of 2-deoxy-scyllo-inosose synthesized according to the method described in WO 2006/112000 and 100 mg of silica gel (Merck Kieselgel 60) were added to 1 mL of water, and the resulting mixture was heated at 150 degrees centigrade for 2 hours. After the completion of the reaction, a quantitative analysis was carried out using HPLC and as a result, (4S,5R,6S)-4,5,6-trihydroxy-2-cyclohexene-1-one was obtained at a yield of 50%. At this time, 15% of the raw material of 2-deoxy-scyllo-inosose was collected.

Analysis conditions for HPLC: 10 mM acetic acid aqueous solution/acetonitrile=94/6, 1.2 mL/min., UV=220 nm, column in use; ODS-AQ, internal standard; methyl gallate.

Example 9

Synthesis of catechol from 2-deoxy-scyllo-inosose 150 mg of 2-deoxy-scyllo-inosose synthesized according to the method described in WO 2006/112000 was dissolved in 3 mL of water, and the resulting mixture was introduced into an autoclave. Furthermore, 7 mg (50 weight % of water contained) of 5 weight % Pd/C was introduced thereinto, and the reactor was replaced with nitrogen. The resulting material was heated to 130 degrees centigrade by applying hydrogen pressure of 0.3 MPa with stirring to conduct a hydrogenation reaction for 3 hours. After cooling, the reactor was replaced with nitrogen and a quantitative analysis was carried out using HPLC. As a result, the raw material was lost, and catechol was obtained at a yield of 29%. Analysis conditions were the same as in Example 1.

Examples 10 to 16

Synthesis of catechol from 2-deoxy-scyllo-inosose

The respective reactions were carried out in the same manner as in Example 9, except that catalysts shown in Table 1 were used instead of 5 weight % Pd/C used in Example 9, and the reaction temperatures and reaction times were changed to those shown in Table 1, and analysis was conducted. Yields of catechol are also shown in Table 1.

TABLE 1

| | Catalyst | | | | | Yield |
| Example | Kind | Amount of metal loaded (weight %) | Weight (mg) | Reaction Temp. (° C.) | Reaction Time (hour) | of catechol (%) |
| --- | --- | --- | --- | --- | --- | --- |
| 10 | Ruthenium/ Activated Carbon | 5 | 1.7 | 130 | 3 | 24 |
| 11 | Rhodium/ Activated Carbon | 5 | 1.3 | 120 | 10 | 43 |
| 12 | Platinum/ Activated Carbon | 2 | 3.8 | 130 | 3 | 35 |
| 13 | Nickel/ Alumina | 40 | 2.0 | 100 | 10 | 23 |

TABLE 1-continued

| Example | Catalyst Kind | Amount of metal loaded (weight %) | Weight (mg) | Reaction Temp. (° C.) | Reaction Time (hour) | Yield of catechol (%) |
|---|---|---|---|---|---|---|
| 14 | Iridium/Activated Carbon | 5 | 7.8 | 100 | 48 | 47 |
| 15 | Palladium/α alumina | 2 | 7.3 | 130 | 3 | 44 |
| 16 | Palladium/Zeolite | 5 | 7.7 | 130 | 3 | 54 |

Example 17

Synthesis of catechol from 2-deoxy-scyllo-inosose 150 mg of 2-deoxy-scyllo-inosose synthesized according to the method described in WO 2006/112000 was dissolved in 3 mL of water, and the resulting mixture was introduced into an autoclave. Furthermore, 1.8 mg (50 weight % of water contained) of 5 weight % Pd/C was introduced thereinto, and the reactor was replaced with nitrogen. The resulting material was heated to 130 degrees centigrade by applying hydrogen pressure of 0.3 MPa with stirring to conduct a hydrogenation reaction for 3 hours. After cooling, the reactor was replaced with nitrogen and a quantitative analysis was carried out using HPLC. As a result, the raw material was lost, and catechol was obtained at a yield of 39%. Analysis conditions were the same as in Example 1.

Example 18

Synthesis of catechol from 2-deoxy-scyllo-inosose>

150 mg of 2-deoxy-scyllo-inosose synthesized according to the method described in WO 2006/112000 was dissolved in 3 mL of water, and the resulting mixture was introduced into an autoclave. Furthermore, 1.5 mg (50 weight % of water contained) of 5 weight % Pd/C and 155 mg of sulfuric acid were introduced thereinto, and the reactor was replaced with nitrogen. The resulting material was heated to 70 degrees centigrade by applying hydrogen pressure of 0.3 MPa with stirring to conduct a hydrogenation reaction for 10 hours. After cooling, the reactor was replaced with nitrogen, and a quantitative analysis was carried out using HPLC. As a result, the raw material was lost, and catechol was obtained at a yield of 41%. Analysis conditions were the same as in Example 1.

Examples 19 to 21

The respective reactions were carried out in the same manner as in Example 18, except that acids shown in Table 2 were used instead of sulfuric acid used in Example 18, and the reaction temperatures were changed to 90 degrees centigrade, and analysis was conducted. Yields of catechol are also shown in Table 2.

TABLE 2

| Examples | Acid | Weight of Acid (mg) | Yield of Catechol (%) |
|---|---|---|---|
| 19 | Trifluoroacetic Acid | 150 | 49 |
| 20 | Dodecylbenzene-sulfonic Acid | 150 | 46 |
| 21 | 47% Hydrobromic Acid | 156 | 25 |

Example 22

Synthesis of catechol from 2-deoxy-scyllo-inosose 150 mg of 2-deoxy-scyllo-inosose synthesized according to the method described in WO 2006/112000 was dissolved in 3 mL of water, and the resulting mixture was introduced into an autoclave. Furthermore, 1.6 mg (50 weight % of water contained) of 5 weight % Pd/C and 152 mg of zeolite Hβ (a product of N.E. Chemcat Corporation) were introduced thereinto, and the reactor was replaced with nitrogen. The resulting material was heated to 130 degrees centigrade by applying hydrogen pressure of 0.3 MPa with stirring to conduct a hydrogenation reaction for 10 hours. After cooling, the reactor was replaced with nitrogen, heated again to 170 degrees centigrade, and stirred for 2 hours. After cooling, a quantitative analysis was carried out using HPLC. As a result, the raw material was lost, and catechol was obtained at a yield of 57%. Analysis conditions were the same as in Example 1.

Example 23

The reaction was carried out in the same manner as in Example 22, except that 155 mg of zeolite HZSM5 (a product of N.E. Chemcat Corporation) was used instead of zeolite Hβ as a solid acid, and analysis was conducted. The results are shown in Table 3.

Example 24

The reaction was carried out in the same manner as in Example 22, except that 153 mg of activated clay (a product of Wako Pure Chemical Industries, Ltd.) was used instead of zeolite Hβ as a solid acid, and analysis was conducted. The results are shown in Table 3.

Example 25

The reaction was carried out in the same manner as in Example 22, except that 155 mg of Nafion (registered trademark) was used instead of zeolite Hβ as a solid acid, and analysis was conducted. The results are shown in Table 3.

TABLE 3

| Examples | Solid Acid Catalyst | Weight of Solid Acid Catalyst (mg) | Yield of Catechol (%) |
|---|---|---|---|
| 23 | Zeolite HZSM-5 | 155 | 54 |
| 24 | Activated Clay | 153 | 49 |
| 25 | Nafion | 155 | 57 |

The invention claimed is:

1. A method for producing catechol from (4S,5R,6S)-4,5,6-trihydroxy-2-cyclohexene-1-one represented by the following formula (1) comprising reacting (4S,5R,6S)-4,5,6-trihydroxy-2-cyclohexene-1-one under hydrogen-reducing conditions while heating

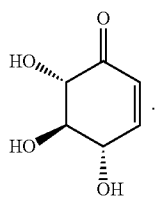

(1)

2. The method for producing catechol as set forth in claim 1, by dehydrating 2-deoxy-scyllo-inosose represented by the following formula (2) to produce (4S,5R,6S)-4,5,6-trihydroxy-2-cyclohexene-1-one, and further conducting hydrogenation and dehydration reactions of the (4S,5R,6S)-4,5,6-trihydroxy-2-cyclohexene-1-one

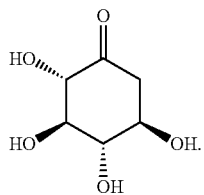

(2)

3. The method for producing catechol as set forth in claim 1, by reacting 2-deoxy-scyllo-inosose under hydrogen-reducing conditions while heating via (4S,5R,6S)-4,5,6-trihydroxy-2-cyclohexene-1-one.

4. The method for producing catechol as set forth in claim 1, by dehydrating 2-deoxy-scyllo-inosose to produce (4S,5R,6S)-4,5,6-trihydroxy-2-cyclohexene-1-one, and further reacting the (4S,5R,6S)-4,5,6-trihydroxy-2-cyclohexene-1-one under hydrogen-reducing conditions while heating.

5. The method for producing catechol as set forth in claim 1, by reacting (4S,5R,6S)-4,5,6-trihydroxy-2-cyclohexene-1-one in the presence of a metal catalyst.

6. The method for producing catechol as set forth in claim 5, wherein said metal catalyst contains a metal selected from the group consisting of platinum group metals or the group consisting of iron group metals.

7. The method for producing catechol as set forth in claim 6, wherein said metal catalyst contains palladium.

8. The method for producing catechol as set forth in claim 5, wherein a metal component contained in said metal catalyst is loaded in activated carbon, alumina or zeolite.

9. The method for producing catechol as set forth in claim 1, by reacting (4S,5R,6S)-4,5,6-trihydroxy-2-cyclohexene-1-one in an aqueous solution.

10. The method for producing catechol as set forth in claim 1, in a one-pot from 2-deoxy-scyllo-inosose.

11. The method for producing catechol as set forth in claim 10, from 2-deoxy-scyllo-inosose in the presence of a solid acid.

12. The method for producing catechol as set forth in claim 11, wherein said solid acid is selected from the group consisting of zeolite, activated clay and perfluoroalkanesulfonic acid resin.

13. The method for producing catechol as set forth in claim 1, by reducing (4S,5R,6S)-4,5,6-trihydroxy-2-cyclohexene-1-one with hydrogen to produce (2S,3R,4S)-2,3,4-trihydroxycyclohexane-1-one represented by the following formula (3), and dehydrating the (2S,3R,4S)-2,3,4-trihydroxycyclohexane-1-one

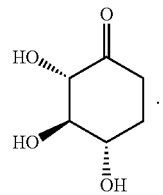

(3)

14. The method for producing catechol as set forth in claim 13, by dehydrating 2-deoxy-scyllo-inosose while heating to give (4S,5R,6S)-4,5,6-trihydroxy-2-cyclohexene-1-one, and then reducing the (4S,5R,6S)-4,5,6-trihydroxy-2-cyclohexene-1-one with hydrogen in the presence of a metal catalyst to give (2S,3R,4S)-2,3,4-trihydroxycyclohexane-1-one, and then further dehydrating the (2S,3R,4S)-2,3,4-trihydroxycyclohexane-1-one while heating.

15. A method for producing (4S,5R,6S)-4,5,6-trihydroxy-2-cyclohexene-1-one by dehydrating 2-deoxy-scyllo-inosose.

16. (4S,5R,6S)-4,5,6-trihydroxy-2-cyclohexene-1-one.

17. A method for producing catechol by dehydrating (2S,3R,4S)-2,3,4-trihydroxycyclohexane-1-one while heating.

18. A method for producing (2S,3R,4S)-2,3,4-trihydroxycyclohexane-1-one by reducing (4S,5R,6S)-4,5,6-trihydroxy-2-cyclohexene-1-one with hydrogen.

19. A method for producing catechol by reacting 2,3,4,5-tetrahydroxy-cyclohexane-1-one represented by the following formula (4) under hydrogen-reducing conditions while heating

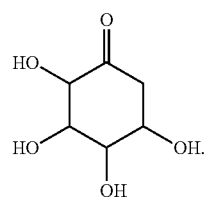

(4)

* * * * *